United States Patent
Rattinger et al.

(10) Patent No.: US 6,174,845 B1
(45) Date of Patent: *Jan. 16, 2001

(54) PERSONAL WASHING BAR COMPOSITIONS COMPRISING EMOLLIENT RICH PHASE/STRIPE

(75) Inventors: Gail Beth Rattinger, Teaneck; Georgia Shafer, Rutherford; James Dalton, Cliffside Park, all of NJ (US); Michael Massaro, Congers, NY (US); Harry Crookham, Lyndhurst, NJ (US); Michael Aronson, West Nyack, NY (US); Terence Farrell, Guttenberg, NJ (US)

(73) Assignee: Lever Brothers Company, division of Conopco, Inc., New York, NY (US)

( * ) Notice: Under 35 U.S.C. 154(b), the term of this patent shall be extended for 0 days.

This patent is subject to a terminal disclaimer.

(21) Appl. No.: 09/302,759

(22) Filed: Apr. 30, 1999

Related U.S. Application Data

(62) Division of application No. 08/828,443, filed on Mar. 28, 1997, now Pat. No. 5,965,501.

(51) Int. Cl.$^7$ .............................. A61K 7/50; C11R 13/00
(52) U.S. Cl. .......................... 510/146; 510/141; 510/152; 510/153; 510/155; 510/156; 510/440; 510/447; 510/451; 510/466; 510/474; 510/484; 510/486; 510/495; 510/504; 510/511
(58) Field of Search ..................... 510/141, 146, 510/152, 153, 155, 156, 440, 447, 451, 466, 474, 484, 486, 495, 504, 511

(56) References Cited

U.S. PATENT DOCUMENTS

| | | |
|---|---|---|
| 3,294,692 | 12/1966 | Kelly et al. . |
| 4,017,574 | 4/1977 | Joshi . |
| 4,224,266 | 9/1980 | Hunt et al. . |
| 5,154,849 | 10/1992 | Visscher et al. . |
| 5,520,840 | 5/1996 | Massaro et al. . |
| 5,540,854 | 7/1996 | Fair et al. . |
| 5,770,556 | * 6/1998 | Farrell et al. ................. 510/447 |
| 5,783,536 | * 7/1998 | Farrell et al. ................. 510/141 |
| 5,817,609 | * 10/1998 | He et al. ....................... 510/133 |
| 5,858,939 | * 1/1999 | Tsaur ............................. 510/141 |
| 5,935,917 | * 8/1999 | Farrell et al. ................. 510/141 |
| 5,955,409 | * 9/1999 | Farrell et al. ................. 510/141 |

FOREIGN PATENT DOCUMENTS

| | | |
|---|---|---|
| 94/03151 | 2/1994 | (WO) . |
| 94/03152 | 2/1994 | (WO) . |

* cited by examiner

*Primary Examiner*—Jill Warden
*Assistant Examiner*—Monique T. Cole
(74) *Attorney, Agent, or Firm*—Ronald A. Koatz

(57) ABSTRACT

The present invention relates to bar compositions in which an emollient composition comprising thickened entrapped emollient is added to a base bar composition at or during time of extrusion to form macroscopic, concentrated domains of emollient droplets. Addition of entrapped droplets allows far greater deposition than if the non-trapped emollients had been mixed in directly to form chips which are then extruded to form final bar.

13 Claims, 1 Drawing Sheet

PERSONAL WASHING BAR COMPOSITIONS COMPRISING EMOLLIENT RICH PHASE/STRIPE

This is a divisional of Ser. No. 08/828,443, filed Mar. 28, 1997 now U.S. Pat. No. 5,965,501, issued Oct. 12, 1999.

FIELD OF THE INVENTION

The present invention relates to bar compositions, particularly (although not exclusively) synthetic soap bar compositions, able to deliver beneficial agents (e.g., silicone) in higher amounts than previously possible. In particular, the invention relates to bar compositions comprising both a base phase and a stripe (emollient containing) phase wherein the stripe phase comprises entrapped emollient droplets (entrapped in that the medium in which the emollient is carried, i.e, polyalkylene glycol, is thickened so that droplets are trapped).

BACKGROUND OF THE INVENTION

It has long been a desirable goal to deliver some kind of benefit agent (e.g., silicone or other oils) to the skin through a personal wash composition.

In liquid cleansers, for example, cationic hydrophilic polymers such as Polymer JR® from Amerchol or Jaguar® from Rhone Poulenc have been used to enhance delivery of benefit agents (EP 93,602; WO 94/03152; and WO 94/03151). In applicants' copending application, U.S. Ser. No. 08/412,803 to Tsaur et al., separate hydrogel particles act as a structure to entrap the benefit agent in concentrated form.

In the subject invention, entrapment of benefit agent is achieved by producing compositions comprising emollient, wherein the medium in which the droplets are found (e.g., polyalkylene glycol) is thickened with a thickening agent (e.g., fumed silica) so that the droplets are entrapped in the polyethylene glycol. The emollient-containing, thickened carrier compositions may be dispersed throughout a bar (as in applicants copending application to Farrell et al. filed on same date as said application) or inserted as a concentrated composition into the bar (e.g., as a stripe).

Delivery of benefit agents (e.g., silicone) has proven difficult in bar compositions for a number of reasons. If the benefit agent does not remain sufficiently discrete from other components in the bar composition, for example, the generally hydrophobic benefit agent will contact hydrophobic materials in the bar mix rather than be free to deposit on the skin or other substrate. Thus, little or no benefit agent will be present in the final bar (after milling, plodding and extrusion of chips) to be delivered to the skin. If the benefit agent is too viscous, it tends to become entangled in the processing equipment and become too difficult to process.

U.S. Pat. No. 5,154,849 to Visscher et al. teaches bar compositions containing a silicone skin mildness/moisturizing aid component. In one embodiment, the silicone component may be mixed with a carrier which is selected to facilitate incorporation of the silicone. Preferred carrier is said to be polyethylene glycol. At column 16, the reference describes that silicone is mixed into melted Carbowax (polyethylene glycol). The mixture is cooled to form flakes and that the flakes are preferably added to an amalgamator.

The compositions of Visscher et al., however, do not teach or suggest thickening the alkylene glycol carrier with a thickening agent (e.g., fumed silica) in order to more readily entrap the emollient. Because the silicone drops are not "contained" by the carrier (e.g., alkylene glycol carrier) in which they are delivered, the benefit agent silicone readily escapes from the carrier and significantly interferes with bar processing (e.g., a viscous, gooey mess is formed which cannot be readily processed) and readily clogs the machinery. By contrast, the entrapped emollient droplets of the invention do not interfere with processing.

Moreover, the present invention is particularly concerned with inserting (e.g., by injection, extrusion or coextrusion) separate compositions comprising the entrapped emollient droplets (i.e., entrapped in the thickened carrier) into bars such that they occupy concentrated regions or domains of the bar (rather than being dispersed as in copending application to Farrell et al., filed on same day). Visscher et al. neither teaches nor suggests concentrated, macroscopic regions of emollient drops from which deposition is enhanced.

Finally in a copending application to He et al., applicants teach low viscosity oils or emollients which are pre-thickened with hydrophobic polymers having low degree of crystallinity. That application teaches thickening of the oils themselves (i.e., thickening low viscosity oils) rather than thickening carriers in which emollients (preferably large size droplet emollients) are found.

SUMMARY OF THE INVENTION

In the subject invention, applicants have unexpectedly found that, when the medium in which emollients are found (i.e., polyalkylene glycol) is thickened with thickening agent, emollient droplets are entrapped in the thickened medium and are able to better deposit emollient from bar compositions. Specifically, the subject invention relates to bar compositions into which the entrapped emollients (present in thickened carrier compositions) are inserted (by injection, extrusion or coextrusion) into a surfactant containing base bar composition to form concentrated regions or domains from which the emollient readily deposits. Said concentrated domains/stripes are macroscopic regions which may range in width from 1 micron($\mu$) to the width of the bar, preferably, $10\mu$ to ½ the width of the bar; and may range in length from $1\mu$ to the length of the bar, preferably being striped along the entire length of the bar. Preferably the emollient containing composition will be striped into the bar as shown in FIG. 1.

Specifically, the invention comprises a bar composition comprising:
  (a) 40% to 99% by wt. of a surfactant selected from the group consisting of soap, anionic surfactants, nonionic surfactants, amphoteric surfactants, cationic surfactants and mixtures thereof; and
  (b) 1% to 60% of a thickened carrier, emollient-containing composition (stripe composition) comprising:
    (1) 20% to 80% by wt. emollient composition polyalkylene glycol;
    (2) 5% to 40% by wt. emollient composition of benefit agent;
    (3) 0.01% to 30%, preferably 5 to 20%, more preferably 5% to 10% thickening agent;
    (4) 0% to 10% by wt. emollient composition water; and
    (5) 0% to 15% by weight emollient composition fatty acid/structure and fillers,
  wherein said stripe composition (b) comprises emollient droplets having average micron size of 5 microns or greater (upper limit defined when drops are no longer dissolved, but continuous) and wherein said entrapped emollient droplets are present in concentrated region (i.e, 1 micron to width of bar by 1 micron to length of bar).

The surfactant system may be a pure soap surfactant system or the surfactant system may comprise:

(a) a first synthetic surfactant which is an anionic surfactant; and (b) a second synthetic surfactant selected from the group consisting of a second anionic different from the first, a nonionic, an amphoteric and mixtures thereof.

A particularly preferred surfactant system comprises acyl isethionate as the first anionic and a sulfosuccinate or a betaine surfactant or mixtures of the two.

DETAILED DESCRIPTION OF THE INVENTION

Figure 1:
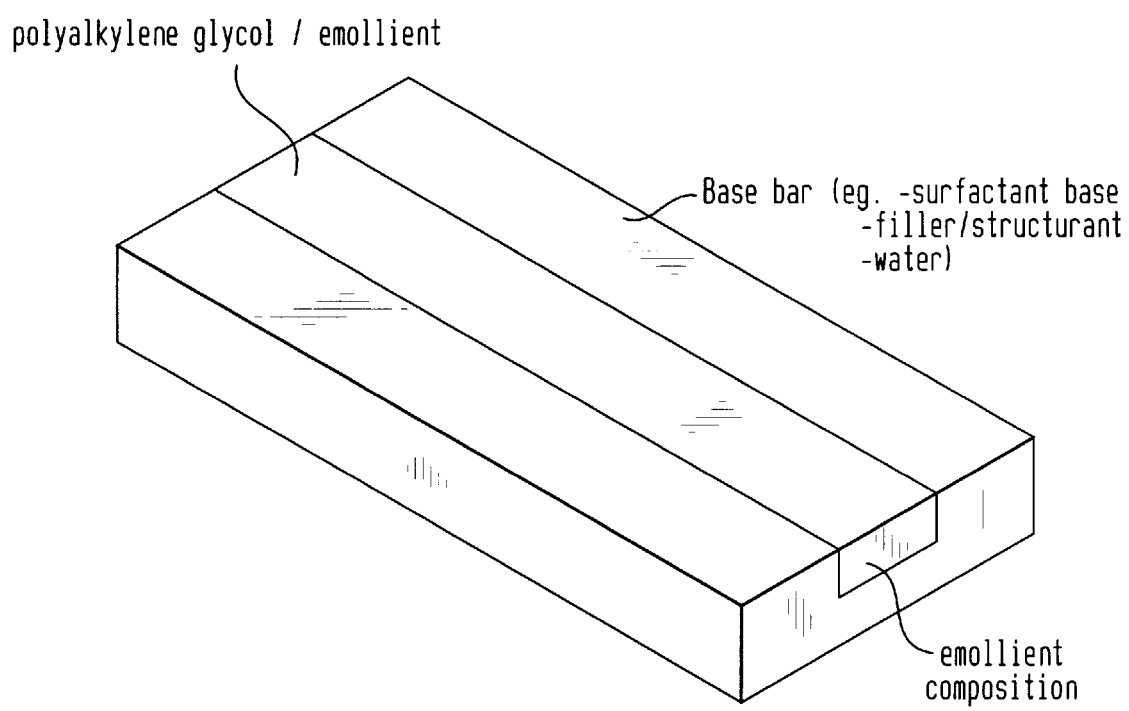
FIG. 1 is a schematic drawing showing a concentrated region/stripe comprising a typical emollient (e.g., silicone) in a thickened polyalkylene glycol carrier added to the rest of the bar composition.

The present invention relates to novel soap bar compositions in which the polyalkylene carrier where emollient is found (emollient droplets have particle size of at least 5$\mu$ and greater) is thickened with a thickening agent such that the viscosity of the carrier is greater than 800 centipoises (cps), preferably greater than 1500 cps and most preferably greater than 3000 cps. The droplets are thereby readily entrapped by the thickened polyalkylene glycol. The emollient containing compositions may also comprise structuring aid/filler, free fatty acid and/or water. The invention further relates to bars in which the emollient containing composition is then inserted into the base bar composition (i.e., surfactant containing portion) forming concentrated, macroscopic regions in which enhanced deposition is found. Enhanced deposition is clearly seen relative to bars in which non-entrapped emollient is added during the mixing, milling and/or refining steps. (Note that applicants copending application, filed on the same day as this application, teaches compositions in which emollients are trapped in thickened carrier, but wherein the carrier is added, preferably as separate composition, by mixing, milling and/or refining)

By using emollient entrapped in thickened carrier, it is believed that the emollient is not free to contact other hydrophobic materials in the bar and is therefore more available to deposit on skin or other substrate.

The invention will now be described in further detail below.

Striped Emollient Composition

Polyalkylene Glycol One component of the emollient phase (stripe) is the polyalkylene glycol carrier. This carrier should comprise about 20% to 80% by wt., preferably about 40% to 70% by wt. of the emollient composition. Preferably, the polyalkylene glycol should have a molecular weight greater than 4,000 to about 100,000, preferably 4000 to 20,000, most preferably 4000–10,000. Minimum MW of about 4000 is believed required so that carrier is solid at room temperature. An especially preferred carrier is polyethylene glycol, for example Carbowax PEG 8000® from Union Carbide.

Benefit Agent

The emollient or benefit agent of the subject invention may be a single benefit agent component, or it may be a benefit agent compound added via a carrier into the process stream. Further the benefit agent may be a mixture of two or more compounds, one or all of which may have a beneficial aspect. In addition, the benefit agent itself may act as a carrier for other components one may wish to add to the bar composition.

The benefit agent can be an "emollient oil" by which is meant a substance which softens the skin (stratum corneum) by increasing water content and keeping it soft by retarding decrease of water content.

Preferred emollients include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids; and (n) mixtures of any of the foregoing components.

A particularly preferred benefit agent is silicone, preferably silicones having viscosity greater than about 50,000 centipoise. One example is polydimethylsiloxane having viscosity of about 60,000 centistokes.

Another preferred benefit agent is benzyl laurate.

The benefit agent generally comprises about 5% to 40% of the emollient-containing composition, preferably 10% to 35%.

Thickening Agent

A critical aspect of the invention is that the polyalkylene glycol carrier is thickened with a thickening agent. While not wishing to be bound by theory, it is the thickening agent which is believed to thicken the carrier such that the emollient droplets stay "immobile" when entrapped within the polyalkylene glycol carrier. As noted in the figures, for example, when thickener is not used, emollient is not "contained" by the polyalkylene glycol carrier and an unprocessable, gooey mess is obtained.

Examples of thickeners which may be used include silica and starches. Among the starches which may be used are water soluble starches such as maltodextrin, polyethylene wax or paraffin wax, or partially soluble starches such as potato or corn starch. By water soluble is meant that a 10% by wt. or greater solution of the starch in water will dissolve to form a clear or substantially clear solution (except for small amounts of insoluble residue which may impart a translucent haziness to otherwise clear solution).

A particularly preferred thickener is fumed silica. Fumed silica is generally produced by the hydrolysis of silicon tetrachloride vapor in a flame of hydrogen and oxygen. The process produces particles of from about 7 to 30 millimicrons.

The enormous surface area and chain forming abilities are believed to allow it to form three-dimensional networks, altering flowing properties i.e., cause thickening.

Thickener will generally comprise the 0.01 to 30% by wt. of the striped composition, preferably 15% to 20% by wt., most preferably 5% to 10% by wt. of the composition.

If fumed silica is the thickener, no more than 10% thickener should be used.

Other Components

Water comprises 0 to 10%, preferably 0% to 8% by wt. of the emollient composition.

In addition the emollient rich phase may comprise 0% to 20%, preferably 2% to 15% fatty acid, i.e., $C_8$ to $C_{24}$ fatty acid. Generally, this is a straight chain, saturated fatty acid although this is not necessarily the case. The fatty acid helps to modify the wear rate of the emollient composition to better match that of the base soap bar composition.

The stripe may further comprise a structuring aid and/or filler which can be a fatty acid as described above or ester derivative; or preferably straight and saturated $C_8$ to $C_{24}$ alcohol or ether derivative.

Bar Phase

The bars of the invention also comprise a bar phase (separate from the emollient composition) which bar phase comprises surfactants, structuring aid/filler, free fatty acid and water.

The surfactant system comprises about 5% to 90% by wt. of a surfactant system wherein the surfactant is selected from the group consisting of soap (pure soap surfactant systems are included), anionic surfactant, nonionic surfactant, amphoteric/zwitterionic surfactant, cationic surfactant and mixtures thereof.

Surfactant System

The term "soap" is used herein in its popular sense, i.e., the alkali metal or alkanol ammonium salts of aliphatic alkane- or alkene monocarboxylic acids. Sodium, potassium, mono-, di- and tri-ethanol ammonium cations, or combinations thereof, are suitable for purposes of this invention. In general, sodium soaps are used int he compositions of this invention, but from about 1% to about 25% of the soap may be potassium soaps. The soaps useful herein are the well known alkali metal salts of natural of synthetic aliphatic (alkanoic or alkenoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are $C_{16}$ and higher. Preferred soap for use in the compositions of this invention has at least about 85% fatty acids having about 12–18 carbon atoms.

Coconut oil employed for the soap may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil, in which case the fatty acid content is about 85% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$), or stearic ($C_{18}$) acids with an alkali metal hydroxide or carbonate.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates.

Sulfosuccinates may be monoalkyl sulfosuccinates having the formula:

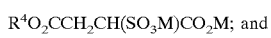

$$R^4O_2CCH_2CH(SO_3M)CO_2M; \text{ and}$$

amide-MEA sulfosuccinates of the formula;

$R^4CONHCH_2CH_2O_2CCH_2CH(SO_3M)CO_2M$ wherein $R^4$ ranges from $C_8$–$C_{22}$ alkyl and M is a solubilizing cation.

Sarcosinates are generally indicated by the formula:

$R'CON(CH_3)CH_2CO_2M$, wherein R ranges from $C_8$–$C_{20}$ alkyl and M is a solubilizing cation.

Taurates are generally identified by formula:

$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of the total bar composition. Preferably, this component is present from about 30% to about 60%.

The acyl isethionate may be an alkoxylated isethionate such as is described in Ilardi et al., U.S. Pat. No. 5,393,466, hereby incorporated by reference. This compound has the general formula:

$$\overset{O}{\underset{\|}{RC}}-O-\overset{X}{\underset{|}{CH}}-CH_2-(O\overset{Y}{\underset{|}{CH}}-CH_2)_{\overline{m}}-SO_3M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1-\overset{O}{\underset{\|}{C}}-NH(CH_2)_{\overline{n}}\!]_n-\overset{R^2}{\underset{\underset{R^3}{|}}{N^+}}-X-Y$$

where $R^1$ is alkyl or alkenyl of 7 to 18 carbon atoms;

$R^2$ and $R^3$ are each independently alkyl, hydroxyalkyl or carboxyalkyl of 1 to 3 carbon atoms;

m is 2 to 4;

n is 0 to 1;

X is alkylene of 1 to 3 carbon atoms optionally substituted with hydroxyl, and

Y is $-CO_2-$ or $-SO_3-$

Suitable amphoteric detergents within the above general formula include simple betaines of formula:

$$R^1-\overset{R^2}{\underset{\underset{R^3}{|}}{N^+}}-CH_2CO_2^-$$

and amido betaines of formula:

$$R^1-CONH(CH_2)_{\overline{n}}-\overset{R^2}{\underset{\underset{R^3}{|}}{N^+}}-CH_2CO_2^-$$

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1-\overset{R^2}{\underset{\underset{R^3}{|}}{N^+}}-(CH_2)_3SO_3^-$$

or $$R^1-CONH(CH_2)_{\overline{m}}-\overset{R^2}{\underset{\underset{R^3}{|}}{N^+}}-(CH_2)_3SO_3^-$$

where m is 2 or 3, or variants of these in which $-(CH_2)_3 SO_3^-$ is replaced by $$-\overset{OH}{\underset{|}{CH_2CHCH_2SO_3^-}}$$

In these formulae $R^1$, $R^2$ and $R^3$ are as discussed previously.

The nonionic which may be used as the second component of the invention include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Examples of cationic detergents are the quaternary ammonium compounds such as alkyldimethylammonium halogenides.

Other surfactants which may be used are described in U.S. Pat. No. 3,723,325 to Parran Jr. and "Surface Active Agents and Detergents" (Vol. I & II) by Schwartz, Perry & Berch, both of which is also incorporated into the subject application by reference.

Although the bar may be a pure soap bar, preferably the surfactant system of this chip (forming the surfactant system in the bar) comprises:

(a) a first synthetic surfactant which is anionic; and
(b) a second synthetic surfactant selected from the group consisting of a second anionic different from the first, a nonionic, an amphoteric and mixtures thereof.

The first anionic can be any of those recited above, but is preferably a $C_8$ to $C_{18}$ isethionate as discussed above. Preferably acyl isethionate will comprise 10% to 90% by wt. total bar composition.

The second surfactant is preferably a sulfosuccinate, a betaine or mixtures of the two. The second surfactant or mixture of surfactant will generally comprise 1% to 10% total bar composition. a particularly preferred composition comprises enough sulfosuccinate to form 3–8% total bar compositions and enough betaine to form 1–5% of total bar composition.

The bar phase also comprises 0.1 to 20% water, preferably 1 to 15% by wt. water.

The bar phase further comprise 0.1 to 80% by wt., preferably 5% to 75% by wt. structuring aid and/or inert filler. Such structurants can be used to enhance the bar integrity, improve the processing properties, and enhance desired user sensory profiles.

The structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurants or fillers include starches, preferably water soluble starches such as maltodextrin and polyethylene wax or paraffin wax.

Structuring aids can also be selected from water soluble polymers chemically modified with hydrophobic moiety or moieties, for example, EO-PO block copolymer, hydrophobically modified PEGs such as POE(200-glyceryl-stearate, glucam DOE 120 (PEG Methyl Glucose Dioleate), and Hodg CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose).

Processing

In general, the chips defining the bar phase are formed by mixing the ingredients of the bar phase in a mixer at a temperature of about 50° C. to 110° C. for 1 to 60 minutes and then cooling in a chill roll. Order of addition is not critical.

The chips may than be refined (e.g., worked into a more pliable mass), plodded or extruded into billets, stamped and cut.

The stripe/emollient composition may be inserted into the base bar composition in a variety of ways including extruding or coextruding this emollient composition into the base composition.

The emollient composition is extruded, for example, into the base bar such that it forms a concentrated domain which may extend from 1 micron to the entire width, preferably $1\mu$ to ½ the width of the bar; and from 1 micron to the entire length of the base bar. An example of this is shown in FIG. 1.

The following examples are intended to further illustrate the invention and are not intended to limit the invention in any way.

Unless stated otherwise, all percentages are intended to be percentages by weight.

EXAMPLES

Protocol

Silicone measurement was conducted as follows:

Analysis is done by method known as ICP (Inductively Coupled Argon Plasma). This procedure required a step involving extraction with xylene, and is therefore currently used only in-vitro. The ICP technique employed a Thermo Jarrell Ash Atom Scan 25 with measurements being made at 251.612 nm. Additional ICP measurement parameters are given below.

The treatment process was as follows:

The porcine skin was shaved, dermatomed, and sectioned into 25 cm pieces prior to treatment. The skin sample was then treated by rubbing the bar sample across the skin 10 times, in a back and forth motion. The resulting liquor on the skin was lathered for 30 seconds and then rinsed for 10 seconds with water which was regulated at 90–95° F. The treated skin sample was placed in a borosilicate scintillation vial that contained 10 ml of xylene. The samples were placed on a platform shaker for 1 hour to allow for the extraction of the silicone. After the extraction period, the skin was removed from the vial and the extract was analyzed using ICP technique. Sample solutions were tested against a 10 pm silicone standard. What is being measured is deposition of silicone (or whatever emollient) in parts per million.

| Typical ICP Measurement Parameters for Measuring Silicone in Xylene | |
|---|---|
| Torch gas flow | high |
| Auxiliary gas flow | 1.5 L/min |
| Analyzer pump rate | 0.9 m L/min |
| Nebulizer pressure | 21 psi |
| Observation height | 12 mm above load cell |
| Plasma power | 1750 W |
| Wavelength | 251.612 nm |
| Slit height | 6 mm |
| Integration time | 4 sec |

Deposition of benefit agent (e.g., silicone) was measured in compositions representing:

(1) soap/synthetic bar in which emollient (silicone) is added to mixer (prior to plodding and extrusion);

(2) soap/synthetic bar composition as in (1) in which entrapped silicone is added as stripe during (coextrusion) or after extrusion;

(3) pure soap bar compositions in which entrapped silicone is added as stripe during extrusion or after extrusion; and (4) a liquid soap composition.

Composition of bars (1) and (2) was a follows:

| COMPONENT | WEIGHT % |
|---|---|
| Alkyl ether sulfonate | 1–5% |
| Soap | 5–10% |
| Acyl Isethionate | 40–60% |
| Alkali metal stearate | 1–5% |
| Water and minors | 10–15% |

Bar (3) was a pure soap bar comprising about 85% to 92% soap and about 8 to 15% water.

Composition of liquid soap (4) was as follows:

| COMPONENT | WEIGHT % |
|---|---|
| Cocoamidopropyl betaine | 5–10% |
| Acyl isethionate | 3–8% |
| Sodium laureth sulfate | 1–3% |
| Silicone | 3–8% |
| Ammonium sulfate | 1–3% |
| Water plus minors | to balance |

The stripe used in formulations (2) and (3) above was as follows:

(1) 56.7% PEG 8000;
(2) 15% polydimethylsiloxane (10,000 centistokes); and
(3) maltodextrin.

The striped bar was prepared as follows:

A soap or syndet bar was carved so that a trough comprises ⅓ of one side of the bar (see FIG. 1). The trough was positioned in the center of one side of, and runs the length of the bar. Cardboard pieces were then secured to the ends of the bar so that they blocked the ends of the trough, forming a mold in which to form the stripe. The molten emollient/polyalkylene glycol material was then poured into the trough and allowed to cool and harden. The cardboard ends were then removed and the surface of the bar containing the stripe was sanded to a flat, smooth finish.

Example 1

Using compositions (1)–(4) described above, deposition results are as follows:

| COMPOSITION | DEPOSITION ($\mu g/cm^2$) |
|---|---|
| Bar (1) Synthetic bar composition (2) Above with 5% non-entrapped PDMS | 0.55 ± 0.33 |
| Bar (2) Synthetic bar composition (2) Above (same composition) with PDMS entrapped in emollient stripe | 1.15 ± 0.58 |
| Bar (3) Pure soap bar (3) described above | 2.03 ± 0.67 |
| Liquid soap composition (4) described above | 2.14 ± 0.62 |

The Table above clearly shows that soap/synthetic bar using stripe deposited for greater amounts of silicone (composition (2) deposing 1.15±0.58 ($\mu g/cm^2$) than the bar prepared without stripes (Composition (1) depositing 0.55±0.33 ($\mu g/cm^1$). Deposition was even greater from pure soap bars (Composition 3) and even reached levels of deposition seen in liquid soaps (4).

Example 2

Applicants used either the soap/synthetic composition of Example 1 as a base or a pure soap base and either extruded/coextruded a benefit stripe or mixed chips and benefit chips, The benefit stripe or chip had the following composition:

33% Benzyl laurate (emollient/benefit agent)
3% Fumed silica; and
64% PEG 8000

Results of deposition (on treated pigskin) were as follows:

| BAR | DEPOSITION |
|---|---|
| Soap/Synthetic Chips Extruded/Coextruded with Benefit Stripe | 11.2 ppm |
| Soap/Synthetic Chips Mixed with Benefit Chips | 14.1 ppm |
| Pure Soap Chips Extruded/Coextruded with Benefit Stripe | 10.4 ppm |

A soap or syndet bar was carved so that a trough comprises ⅓ of one side of the bar (see FIG. 1). The trough was positioned in the center of one side of, and runs the length of the bar. Cardboard pieces were then secured to the ends of the bar so that they blocked the ends of the trough, forming a mold in which to form the stripe. The molten emollient/polyalkylene glycol material was then poured into the trough and allowed to cool and harden. The cardboard ends were then removed and the surface of the bar containing the stripe was sanded to a flat, smooth finish.

This example clearly shows that silica such as fumed silica, may also be used as polyalkylene glycol thickening materials.

Example 3

Applicants again used either a pure soap or a synthetic soap base to be combined with benefit stripe or benefit chips.

When stripes were used, stripe formulation was as follows;

30% PDMS 100,000 (silicone emollient)
23% Maltodextrin (thickener); and
46.7% PEG When benefit chips were used, formulation was as follows:

33% PDMS 100,000
3% Fumed silica
64% PEG

Chips were incorporated at 30% of bar.

In addition the liquid formulation of Example 1 was used to compare.

Results on pigskin treated with formulation were as follows:

| FORMULATION | DEPOSITION |
|---|---|
| Soap/Synthetic with Stripe | 13.9 ppm |
| Pure Soap with Benefit Stripe | 28.0 ppm |
| Soap/Synthetic with Benefit Chips | 6.5 ppm |
| Liquid Soap | 2.14 ppm |

The results clearly showed both strong deposition relative to liquid as well as superior deposition using stripe. Deposition from pure soap bar was much better than for soap/synthetic. Higher deposition results relative to Example 1 are due to variations in one set of tests versus another. The important thing, however, is the differences demonstrated within the same set of tests since these are all subject to same day to day conditions.

Example 4

Fatty acid was incorporated in a pure soap bar using following stripe material:
30% PDMS 100,000
40% PEG 8000
20% Maltodextrin
10% Fatty acid (stearic/palmitic blend)

Using same measurement technique, the following results were found:

| BAR | DEPOSITION |
|---|---|
| Pure Soap with Stripe (no fatty acid) | 52.63 ppm |
| Pure Soap with Stripe (including fatty acid) | 17.63 ppm |

This example shows that hydrophobic materials can be added (e.g., to help wear rate) without eliminating deposition.

What is claimed is:

1. A bar composition comprising:
   (a) 40% to 99% by wt. of a bar phase comprising;
      (1) 5 to 90% of bar phase surfactant system;
      (2) 0.1 to 20% of bar phase water;
   (b) 1% to 60% by wt. of a striped emollient composition comprising:
      (1) 20–80% polyalkylene glycol carrier;
      (2) 5–40% emollient;
      (3) 0.1–30% thickening agent;
      (4) 0–10% water; and
      (5) 0–15% structurant/filler;
   wherein said emollient (b)(2) is in the form of droplets entrapped in said carrier (b)(1) thickened with a thickening agent (b)(3) such that viscosity of said carrier is equal to or greater than 8000 cps;
   wherein said emollient droplets have size of at least 5 microns; and
   wherein said entrapped emollient droplets are concentrated to form domains when said carrier which contains the droplets is injected, extruded, coextruded, or otherwise inserted into said bar composition;
   wherein said domains are 1 micron to the width of bar in width and 1 micron to length of bar in length.

2. A composition according to claim 1, wherein the surfactant system comprises:
   (a) a first synthetic surfactant which is anionic; and
   (b) a second synthetic surfactant selected from the group consisting of a second anionic different from the first, a nonionic, an amphoteric and mixtures thereof.

3. A composition according to claim 2, wherein first anionic is acyl isethionate.

4. A composition according to claim 2 wherein second surfactant is an amphoteric surfactant selected from the group consisting of sulfosuccinate, betaine and mixtures thereof.

5. A composition according to claim 1, wherein carrier is polyalkylene glycol having MW 4000 to 100,000.

6. A composition according to claim 5, wherein molecular weight is 4,000 to 20,000.

7. A composition according to claim 6, wherein molecular weight is 4,000 to 10,000.

8. A composition according to claim 1, wherein thickening agent is fumed silica.

9. A composition according to claim 1, wherein thickening agent is a water soluble starch.

10. A composition according to claim 9, wherein said starch is maltodextrin.

11. A composition according to claim 1, wherein bar phase additionally comprises a structurant/filler selected from the group consisting of $C_8$–$C_{20}$ fatty acid or ester derivative; $C_8$–$C_{24}$ alcohol or ether derivative thereof, polyalkylene glycol of MW 2000–20,000, starch and wax.

12. A composition according to claim 1, wherein viscosity of thickened carrier is greater than about 1500 cps.

13. A composition according to claim 12, wherein viscosity is greater than 3000 cps.

* * * * *